United States Patent
Brenkman et al.

[11] Patent Number: 5,674,830
[45] Date of Patent: Oct. 7, 1997

[54] PROCESS FOR THE PREPARATION OF ALKYLGLYCOSIDE ESTERS

[75] Inventors: Tanja Brenkman, Reeuwijk, Netherlands; Alasdair R. Macrae, Newton Blossomville; Richard E. Moss, Little Neston, both of United Kingdom

[73] Assignee: Unichema Chemie B.V., Gouda, Netherlands

[21] Appl. No.: 367,113
[22] PCT Filed: Jun. 25, 1993
[86] PCT No.: PCT/EP93/01645
  § 371 Date: May 31, 1995
  § 102(e) Date: May 31, 1995
[87] PCT Pub. No.: WO94/01575
  PCT Pub. Date: Jan. 20, 1994

[30] Foreign Application Priority Data

Jul. 7, 1992 [EP] European Pat. Off. ............ 92306224

[51] Int. Cl.$^6$ ........................... C11D 3/22; C12N 9/14
[52] U.S. Cl. ................. 510/470; 510/392; 435/74; 435/174; 536/4.1
[58] Field of Search .................. 435/74, 174; 536/4.1; 252/174.12, 95; 510/470, 392

[56] References Cited

U.S. PATENT DOCUMENTS

| | | | |
|---|---|---|---|
| 4,614,718 | 9/1986 | Seino et al. | 435/72 |
| 4,839,287 | 6/1989 | Holmberg et al. | 435/135 |
| 4,959,459 | 9/1990 | David et al. | 536/1.1 |
| 5,200,328 | 4/1993 | Kirk et al. | 435/101 |

FOREIGN PATENT DOCUMENTS

| | | |
|---|---|---|
| 0334498 | 9/1989 | European Pat. Off. |
| 0413307 | 2/1991 | European Pat. Off. |
| 2-242692 | 9/1990 | Japan |
| 9401575 | 1/1994 | WIPO |

*Primary Examiner*—Paul Lieberman
*Assistant Examiner*—Kery A. Fries
*Attorney, Agent, or Firm*—Cushman Darby & Cushman IP Group Pillsbury Madison & Sutro LLP

[57] ABSTRACT

In a process for the manufacture of $C_1$–$C_{18}$ alkylglycoside ester of $C_4$–$C_{24}$ fatty acids, the reactants are first formed into a stable micro-emulsion before they are contacted with an enzyme catalyst. The stable micro-emulsion is prepared, using a surface-active material, which is preferably the alkylglycoside ester formed.

20 Claims, No Drawings

PROCESS FOR THE PREPARATION OF ALKYLGLYCOSIDE ESTERS

The present invention relates to a process for the manufacture of alkylglycoside esters, in which an alkylglycoside and an acyl group donor are contacted with an enzyme catalyst.

Such a process is known from e.g. PCT patent applications WO-B-8901480 and WO-B-9009451, as well as from Synthesis, February 1990, pp. 112–115 and J. Chem. Soc., Chem. Commum., 1989, pp. 934–935.

In these publications, processes are described for the enzyme catalysed preparation of 6-0-acylglucopyranosides by simply mixing the starting alkylglycoside with a fatty acid at 70° C. in the presence of an immobilized lipase. The water generated in the reaction is removed in vacuo. In this way, using a species of *Candida antarctica*, yields of 85–95% of the 6-0-monoesters were obtained. Although a suitable solvent, such as hexane or acetonitrile may be used, such solvent will generally inactivate the enzyme, and they are toxic, which is detrimental to the environment and requires a thorough purification of the end product, if this has to be used in food or cosmetic applications.

A problem in the processes thus described is the high viscosity of the alkylglycoside, which needs to be mixed with the molten fatty acid, which is very difficult and increases the total reaction time considerably. Also if the amount of acyl donor is increased relative to the alkylglycoside to increase the reaction efficiency, by-products, such as diesters tend to be formed in appreciable amounts.

There is therefore still a need for a process for the manufacture of alkylglycoside esters having a high monoester content at a high reaction rate, without the problems as outlined above.

It is an object of the present invention to provide a process for the manufacture of alkylglycoside esters, in which an alkylglycoside and an acyl group donor are contacted with an enzyme catalyst, in which in a relatively short time alkylglycoside monoesters of high purity are formed.

During extensive investigations it has been found that if the alkylglycoside and the acyl donor are mixed with a surface active material, preferably with an effective amount of the alkylglycoside ester formed, a stable micro-emulsion is formed, which is very easy to handle throughout the whole manufacturing process. By "a micro-emulsion" is understood throughout this specification and the attached claims a dispersed system stabilized by surfactants which could be micellar systems or true micro-emulsions. By changing the ratio of acyl donor to alkylglycoside it appeared to be possible to control the viscosity of the micro-emulsion, whereas the stability of the micro-emulsion could be controlled by the amount and (to a lesser extent) the type of surface-active material used. A molar ratio of acyl donor to alkylglycoside of 1.0–2.0 moles of acyl donor per mole of alkylglycoside is preferred.

It has been stated in U.S. Pat. No. 4,614,718 (Seino et al.) that sugar or sugar-alcohol fatty acid esters have been prepared by dispersing a lower alkyl ester of a fatty acid in a solution of sugar in a solvent, such as propylene glycol or water, with the aid of an emulsifier, such as soap, after which the solvent is removed before the transesterification reaction is started. This process is said to be known as the "micro-emulsion process" (see U.S. Pat. No. 4,614,718, Column 1, lines 17–22). This is a non-enzymatic process, however, and Seino et al. clearly state that this method exhibits serious disadvantages, such as the high reaction temperature, leading to discoloration and the use of solvents. The "micro-emulsion process" has been described in detail in Journal of the American Oil Chemists' Society, Volume 44, No. 5 (May 1967), 307–309. In this publication it has been described how sucrose dissolved in propylene glycol, methyl stearate, sodium stearate and potassium carbonate catalyst are combined to form a transparent micro-emulsion. On page 309 it has been stated that this micro-emulsion is formed at 130°–135° C., and that the micro-emulsion is not stable at room temperature.

In the process according to the present invention the micro-emulsions can be formed at room temperature and they are indefinitely stable. This stability is an advantage because it is possible to preform the micro-emulsion and then store it, without any danger that it will change in character or composition through precipitation or phase separation. Also no heating treatment is required which may impair the colour of the product.

Also in the Osipow et al. process the solvent is left in the system until it is distilled out during the course of the reaction, and moreover potassium carbonate is used, which helps to form the anionic surfactant needed to stabilise the micro-emulsion and which is essential as a catalyst. In the process of the present invention the catalyst has no role whatsoever in the micro-emulsion process and the solvent is removed, to leave a very stable micro-emulsion.

Therefore the present invention relates to a process for the manufacture of alkylglycoside esters, in which an alkylglycoside and an acyl group donor are contacted with an enzyme catalyst, which is characterized in that a stable micro-emulsion is formed from the reactants, before the reactants are contacted with the enzyme catalyst using a surface-active material.

The stable micro-emulsion of the reactants can be prepared in a number of ways, which are to a certain extent dictated by the type and relative amounts of the reactants. It is possible to take the acyl donor and the alkylglycoside, add the surface-active material and to stir the mixture obtained vigorously. Dependent on the type of alkylglycoside and the acyl donor and their relative amounts, this will still take some time due to the viscous nature of the alkylglycoside, but already an improvement in the process is obtained in this way, because of the high contact surface offered by the micro-emulsion to the enzyme catalyst in the next step of the process.

It has been found advantageous, however, to dissolve the alkylglycoside, the acyl donor and the surface-active material in a common solvent, which is preferably innocuous, such as ethanol, whilst stirring. When the solvent is evaporated from the homogeneous solution, the micro-emulsion forms spontaneously. The evaporated solvent can be condensed and recycled into the process. Suitable solvents are the lower alkanols having up to four carbon atoms and polyhydric alcohols, such as glycols, or glycerol, but preferably a solvent is used having a boiling point below about 100° C., which is innocuous. The micro-emulsion is preferably formed between room temperature (15° C.) and 80° C.

In a particularly preferred embodiment of the present invention, an excess of alcohol is used in the previous production of the alkylglycoside, so that a mixture of alkylglycoside and alcohol is obtained. This mixture is then mixed with the acyl donor and the surface-active material (preferably the alkylglycoside ester formed) and whilst stirring, the excess alcohol is then removed by distillation or evaporation, after which a stable micro-emulsion is obtained. Thus, for example, with 5% by weight of ethylglucoside dodecanoic acid ester, dodecanoic acid and ethylglucoside, finally an emulsion was obtained having a viscosity of 300–400 cP at 60–80° C.

Preferably the surface-active material is the alkylglycoside ester which is formed in the process and an effective amount of the ester formed is continuously recycled into the process for the formation of the stable micro-emulsion.

It is also possible to form the stable micro-emulsion, using other, preferably nonionic and/or anionic surface-active agents, such as fatty acid monoglycerides, polyglycerol fatty acid esters, fatty acid sodium or potassium soaps, sugar esters, sugar alcohol esters; sodium bis(2-ethylhexyl) sulfosuccinate; other alkylglycoside esters than those formed in the reaction; alkylpolyglycosides and mixtures thereof.

Preferably the surface-active agent or mixture thereof is innocuous or food grade. In general no surface-active agents are used which under the conditions of the reaction will participate in the reaction.

After the micro-emulsion has been formed, the enzyme catalyst can be added to it whilst stirring and keeping the mixture at about 30° C. to 80° C., whilst also applying a vacuum to remove the water produced in the esterification reaction. The reaction mixture can, for example, be circulated through an external evaporator (falling or wiped film reactor) to facilitate the removal of the water of esterification, but also to remove the alcohol used in the formation of the micro-emulsion.

It is known to immobilize enzyme catalysts, which usually includes cross-linking of cell homogenates, coating on a solid particulate support, such as plastics, polysaccharides, ion exchange resins, silicates (glass), entrapment in gels and the like. Such immobilized enzyme catalysts have the advantage of being easily to separate. Surprisingly, the present invention enables the use of the enzyme catalyst in the form of a solution or dispersion. The use of the micro-emulsion will allow easy and highly effective dispersion of the enzyme catalyst in the reaction mixture, with almost each enzyme molecule in a different micro-emulsion droplet. This leads to fast reaction rates with a high degree of conversion.

It has been disclosed in European Patent Application EP-A-0,334,498 (Cerestar Holding BV) to prepare esters of alkylglucosides by using a non-immobilised enzyme catalyst, but first of all, the reaction times vary from 24 to 120 hours and more important the yields are not higher than 50%.

The reaction technique as embodied by the present invention does lead to short reaction times and very high yields of almost pure product.

The enzyme catalyst is a catalyst which is active in the hydrolysis of ester bonds and therefore is a hydrolase. The enzyme catalyst preferably is selected from the group consisting of lipases (e.g. porcine pancreas lipase or microbial lipases), esterases or proteases. The use of thermostable lipases, such as derived form *Candida antarctica* as described in PCT application WO-B-8802775 (Novo Industri) or derived from *Mucor miehei* is preferred.

If the enzyme catalyst is used in immobilized form, a preferred embodiment of the process according to the present invention is to form the micro-emulsion of the reactants with the surface-active material, preferably from a starting solution in a common solvent as referred to earlier, after which the micro-emulsion is pumped through one or more beds packed with the enzyme catalyst immobilised on a suitable support material. Between the reactors, the water produced in the reaction is removed, suitably by passing the reaction mixture through a falling or wiped film evaporator, to ensure that the esterification reduction reaches the required, high degree of conversion. This embodiment, using a packed bed reactor would, without the use of the micro-emulsion technique according to the present invention technically not have been feasible.

The alkyl group of the alkylglycoside may be a saturated or unsaturated, straight or branched chain alkyl group, having from 1 to 18 carbon atoms. The alkyl group may be substituted with functional groups, such as hydroxyl groups. The use of a saturated, straight chain alkyl group, having from 1 to 8 carbon atoms is preferred.

The glycoside part of the alkylglycoside comprises from 1 to 3 monosaccharide units. These monosaccharide units preferably are in the pentose or hexose from (particularly the furanose or pyranose form). Suitable monosaccharides are arabinose, ribose, xylose, xylulose, lyxose, rubulose and 2-deoxyribose, glucose, fructose, galactose, mannose, sorbose, talose and deoxy sugars, such as 2-deoxyglucose, 6-deoxygalactose, 6-deoxymannose and 2-deoxygalactose. Preferred disaccharides are maltose, isomaltose, sucrose, cellobiose, lactose and sophorose. Also various hepturoses, such as glucohepturose, arohepturose, sidohepturose and mannohepturose may be used. Mixtures of alkylglycosides may also be used.

The acyl group donor is selected from the group consisting of saturated or unsaturated, straight or branched chain fatty acids having from 4 to 24 carbon atoms. The fatty acids may also comprise functional groups, such as hydroxyl groups, halogen atoms and like other groups.

Another group of acyl donors are the esters of the said of fatty acids with alkanols having from 1 to 8 carbon atoms. Finally the acyl group donor may be a monoglyceride, diglyceride and/or triglyceride of the said fatty acids. Mixtures of acyl group donors may also be used. The use of free fatty acids and $C_1$–$C_3$ alkyl esters of said fatty acids is preferred.

Also fatty acid oxime esters can be used as the acyl donors.

The reaction temperature at which the reactants micro-emulsion is contacted with the enzyme catalyst ranges from 20° C. to 110° C., preferably from about 30° C. to 80° C.

In order to remove any solvent or the water of esterification formed in the reaction, the process according to the present invention is preferably carried out at sub-atmospheric pressure (vacuum).

The alkylglycoside esters prepared by means of the process according to the present invention may advantageously be use in detergent compositions, in cosmetic products and compositions and in foodstuffs or food additive compositions.

The invention is now further illustrated by the following examples.

EXAMPLE I

In this example the generation of stable micro-emulsions from ethylglucoside, fatty acid and surfactant has been described.

A mixture of 60 g lauric acid, 52 g of ethylglucoside and 5.6 g of a surfactant were dissolved in 100 ml of ethanol. The solvent was then evaporated from the mixture using a rotary evaporator and the stability of the mixture left, when all the solvent had been removed, was assessed. When a stable micro-emulsion system is formed, the system remains homogeneous, whereas in cases where no micro-emulsion is formed, it can be clearly seen that the system separates into two distinct phases.

The following surfactants were found to give stable micro-emulsions:

alkylpolyglucosides, made from decanol and dodecanol with an average degree of polymerization of the polyglucoside of 1.4; 20 grams of a 28 wt % solution of sodium lauryl ethersulphate in water; sodium lauryl sulphate; sodium dihexylsulphosuccinate.

EXAMPLE II

A solution of an alkylpolyglucoside (33 g, derived from directly from decanol and glucose by a standard procedure as described in U.S. Pat. No. 3,839,318) in ethanol (50 ml) was added to a mixture of ethylglucoside (312 g) and lauric acid (360 g) contained in a round bottomed flask fitted with a stirrer and a condenser.

A further portion of ethanol (100 ml) was added and the mixture was warmed to 70° C. and maintained at this temperature until all the materials had dissolved. Once the solution was homogeneous the ethanol was removed, by distillation, and supported lipase enzyme (SP 435, ex Novo Nordisk A/S, 33 g slurried with 33 mls water) was added to the resulting homogeneous mixture.

After the enzyme had been added, the reaction mixture was heated to 75° C. and stirred under vacuum to remove the water formed in the esterification reaction. The reaction was followed by HPLC and after 23 hours reaction time 80% conversion of the ethylglycoside to the ester was seen.

EXAMPLE III

A solution of ethylglucoside (30%) in ethanol (500 kg ethylglycoside) was pumped into an autoclave fitted with a condenser, vacuum system and stirrer and the ethanol was removed by distillation to leave a viscous syrup. Molten lauric acid (540 kg, Unichema Prifac 2922; ™) was added and the mixture was maintained at 70° C. and stirred for 4 hr after which the reagents were still not fully mixed. A thick layer of ethylglucoside remained in the bottom of the autoclave. Enzyme (Novo SP 435, 50 kg) was added and the system was maintained at 75° C. under vacuum (10 mbar) for 24 hours. After 6 h the reaction mixture was homogeneous and analysis by HPLC showed that the ethylglucoside was converted to the lauric acid ester (85% conversion after 15 h). This example clearly shows the advantage of generating the homogeneous micro-emulsion in solution.

EXAMPLE IV

The procedure of Example III was repeated with the following changes: before the alcohol was distilled from the ethylglucoside, 50 kg of the ester, prepared in the previous reaction was added. The fatty acid was added as the alcohol was distilled from the reactor and at the end of the distillation the reaction mixture was a mobile syrup that could be stirred without difficulty.

EXAMPLE V $C_{12}$ fatty acid ethylglucoside ester (13.0 g) and ethylglucoside (112.0 g) were weighed into a 500 ml round-bottom vessel and mixed at 80° C. by stirring with an impeller. Lauric acid (130.4 g) (Prifrac 2920, ex Unichema International Trade Mark) was added to the vessel and further stirring for 2 hours at 80° C. and a pressure of 20 mbar produced a micro-emulsion and, in addition, removed residual ethanol from the reaction mixture. At this point samples were removed from the vessel for analysis by HPLC and for acid value determination.

The temperature of the reaction mixture was reduced to 60° C. and the pressure to 10 mbar. A solution of *Candida antarctica* lipase B (800 mg) (SP 434, ex. Novo Nordisk, activity=200 KLU/g) in distilled water (6 ml) was added to the contents of the vessel. Stirring (at 250 rpm) was continued and further samples were removed for HPLC analysis and for acid value determination if required. The reaction was terminated after 23 hours. The compositions of the reaction mixture in wt % at various reaction times are given in Table 1. After 23 hours the yield of ethylglucoside ester was 90% based on ethylglucoside.

Samples taken for analysis by HPLC were weighed into vials. After a cap had been fitted, each vial was immersed in boiling water for at least 30 minutes to deactivate the enzyme in the sample. The deactivated samples were dissolved in known amounts of 96% aqueous ethanol and analysed by HPLC to determine the concentration of ethylglucoside ester and ethylglucoside in each sample.

TABLE 1

| Reaction Time (hours) | EGE (wt %) | EG (wt %) | LA (wt %) |
| --- | --- | --- | --- |
| 0 | 4.2 | 37.8 | 51.1 |
| 1.0 | 13.0 | 30.6 | — |
| 2.0 | — | — | — |
| 2.5 | 28.2 | 26.4 | — |
| 3.0 | — | — | — |
| 3.5 | 34.0 | 23.8 | — |
| 4.0 | — | — | |
| 4.5 | 40.5 | 18.2 | — |
| 5.0 | — | — | — |
| 5.5 | 43.9 | 17.0 | — |
| 6.0 | — | — | — |
| 23.0 | 67.3 | 4.5 | 26.1 |

NB EGE = $C_{12}$ ethylglucoside ester
EG = ethylglucoside
LA = lauric acid

The rate of synthesis of ester over the first five hours is approximately linear with respect to time and was over this time period 67 mmol ester/hour/g of enzyme.

EXAMPLE VI

Example V was repeated, but in this experiment, an amount of the ester product was not added to the vessel prior to the addition of the enzyme. Therefore, a micro-emulsion did not form in the reaction mixture until a requisite amount of ester had been synthesised in the vessel. As with the first experiment, a lauric acid: ethylglucoside molar ratio of 1.2:1 was employed.

Ethylglucoside (112.5 g) and lauric acid (131 g) were weighed into a round-bottom vessel. Residual ethanol was removed as before by stirring for 2 hours at 80° C. and 20 mbar. *Candida antarctica* lipase B (800 mg) in distilled water (6 ml) was added and contents of the vessel were stirred at 60° C. and about 15 mbar. Initially, the viscosity of the reaction mixture was too high for samples to be removed by pipette for analysis. However, from two hours onwards samples were taken following a reduction in viscosity. The compositions of the reaction mixture at various reaction times are given in Table 2.

After 23 hours the yield of ethylglucoside ester was about 90% based on ethylglucoside. Then also the rate of synthesis of ester over the first five hours is approximately linear with respect to time, but the rate over this period was 50 mmol ester/hour/g of enzyme, suggesting a faster reaction rate by the formation of a micro-emulsion prior to the addition of enzyme.

TABLE 2

| Reaction Time (hours) | EGE | EG | LA |
|---|---|---|---|
| 0 | 0 | 39.3 | 53.8 |
| 1.0 | — | — | — |
| 2.0 | 13.2 | 31.4 | — |
| 2.5 | — | — | — |
| 3.0 | 19.6 | 28.0 | — |
| 3.5 | — | — | — |
| 4.0 | 25.5 | 24.9 | — |
| 4.5 | — | — | — |
| 5.0 | 31.2 | 23.0 | — |
| 5.5 | — | — | — |
| 6.0 | 35.9 | 20.9 | — |
| 23.0 | 67.9 | 5.6 | 26.4 |

NB EGE = $C_{12}$ ethylglucoside ester
EG = ethylglucoside
LA = lauric acid

We claim:

1. In a process for the manufacture of alkylglycoside esters, in which an alkylglycoside and an acyl group donor are contacted with an enzyme catalyst, the improvement wherein a stable micro-emulsion is formed by mixing the reactants and surface-active material before the reactants are contacted with the enzyme catalyst and only thereafter contacting the enzyme with said micro-emulsion.

2. A process according to claim 1 wherein the stable micro-emulsion of the reactants is formed by using an amount effective to form said micro-emulsion of the produced alkylglycoside ester as the surface-active material.

3. A process according to claim 1, wherein the surface-active material is selected from the group consisting of fatty acid monoglycerides, polyglycerol fatty acid esters, sugar alcohol esters, alkylglycoside esters, alkylpolyglycosides, and mixtures thereof.

4. A process according to claim 1, wherein the stable micro-emulsion of the reactants is formed by dissolving the acyl group donor, the alkylglycoside and the surface-active material in the same solvent, after which the solvent is removed from the homogeneous solution.

5. A process according to claim 4, wherein the solvent is selected form the group consisting of $C_1$-$C_4$ alkanols, polyhydric alcohols, and mixtures thereof.

6. A process according to claim 1, in which the micro-emulsion is formed between room temperature and 80° C.

7. A process according to claim 1, wherein the stable micro-emulsion is contacted with an immobilized enzyme.

8. A process according the claim 1, wherein the stable micro-emulsion is contacted with an enzyme immobilized in the form of a packed bed.

9. A process according to claim 1, wherein the enzyme catalyst is dispersed in the form of a solution or dispersion into the stable micro-emulsion.

10. A process according to claim 1, wherein the enzyme catalyst is a hydrolase.

11. A process according to claim 1, wherein the enzyme catalyst is selected form the group consisting of lipases, esterases, proteases and mixtures thereof.

12. A process according to claim 1, wherein the alkyl group of the alkylglycoside is a saturated or unsaturated, straight or branched chain alkyl group having 1–18 carbon atoms.

13. A process according to claim 1, wherein the alkyl group of the alkylglycoside is a saturated, straight chain alkyl group having 1–8 carbon atoms.

14. A process according to claim 1, wherein the glycoside part of the alkylglycoside comprises 1–3 monosaccharide units.

15. A process according to claim 1, wherein the glycoside part of the alkylglycoside is selected form the group consisting of glucose, fructose, galactose, xylose, ribose, mannose, arabinose, lactose, maltose, isomaltose, sucrose, cellobiose, arabinose, xylulose, rubulose, 2-deoxyribose, sorbose, talose, 2-deoxyglucose, 6-deoxyglucose, 6-deoxymannose, 2-deoxygalactose, sophorose, arohepturose, sedohepturose, mannohepturose, glucohepturose and mixtures thereof.

16. A process according to claim 1, wherein the acyl group donor is selected from the group consisting of saturated or unsaturated, straight or branched chain $C_4$-$C_{24}$ fatty acids, $C_1$-$C_8$ alkyl esters of said fatty acids, glycerol esters of said fatty acids, and mixtures thereof.

17. A process according to claim 1, wherein the reactants are contacted with the enzyme catalyst at a temperature of from 20° C. to 110° C.

18. A process according to claim 1, wherein the reactants are contacted with the enzyme catalyst at sub-atmospheric pressure.

19. A process according to claim 17 wherein the temperature of contact is from 30° C. to 80° C.

20. A process according to claim 1 wherein the micro-emulsion consists of the alkylglycoside, acyl group donor and surface-active material.

* * * * *